United States Patent [19]

Tolman et al.

[11] Patent Number: 4,966,895

[45] Date of Patent: Oct. 30, 1990

[54] CYCLIC MONOPHOSPHATES OF PURINE AND PYRIMIDINE ACYCLONUCLEOSIDES AS ANTI-RETROVIRAL AGENTS

[75] Inventors: Richard L. Tolman, Warren; Malcolm MacCoss, Freehold, both of N.J.

[73] Assignee: Merck & Co. Inc., N.J.

[21] Appl. No.: 305,234

[22] Filed: Feb. 2, 1989

[51] Int. Cl.$^5$ .......................................... A61K 31/675
[52] U.S. Cl. ...................................... 514/81; 514/86
[58] Field of Search .......................................... 514/110

[56] References Cited

U.S. PATENT DOCUMENTS

| | | | |
|---|---|---|---|
| 4,199,574 | 4/1980 | Schaeffer | 544/229 |
| 4,287,188 | 9/1981 | Schaeffer | 544/244 |
| 4,323,573 | 4/1982 | Schaeffer | 544/244 |
| 4,495,190 | 1/1985 | Hagberg et al. | 514/262 |
| 4,565,868 | 1/1986 | Verheyden | 514/262 |
| 4,579,849 | 4/1986 | MacCoss et al. | 514/262 |
| 4,590,269 | 5/1986 | Prisbe et al. | 514/261 |
| 4,670,424 | 6/1987 | MacCoss et al. | 514/81 |

FOREIGN PATENT DOCUMENTS

| | | |
|---|---|---|
| 82107247.7 | 2/1983 | European Pat. Off. . |
| 82401571.3 | 3/1983 | European Pat. Off. ............ 514/110 |
| 83100886.7 | 8/1983 | European Pat. Off. . |
| 84401311.0 | of 1985 | European Pat. Off. . |
| 84108630.1 | 5/1985 | European Pat. Off. . |
| 84109539.1 | 5/1985 | European Pat. Off. . |
| 85400087.4 | 8/1985 | European Pat. Off. . |
| 86305586.9 | 4/1986 | European Pat. Off. . |
| 86302822.9 | 12/1986 | European Pat. Off. . |
| 72-25358 | 7/1972 | Japan . |
| 84/00167 | 1/1984 | PCT Int'l Appl. . |

OTHER PUBLICATIONS

Bailey et al., J. Chem. Soc., pp. 2767–2775 (1988).
Pandit et al., Synthetic Communications, 2(6)345–351 (1972)

*Primary Examiner*—Jerome D. Goldberg

[57] ABSTRACT

The present invention relates to a method for treating mammals having acquired immuno-deficiency syndrome (AIDS) or AIDS-related complex or who are infected with other retroviruses, which comprises the administration of a therapeutically effective amount of a cyclic monophosphate derivative of a purine or pyrimidine acyclonucleoside. Process for the preparation of such compounds and compositions containing such compounds as the active ingredient thereof are also disclosed.

2 Claims, No Drawings

CYCLIC MONOPHOSPHATES OF PURINE AND PYRIMIDINE ACYCLONUCLEOSIDES AS ANTI-RETROVIRAL AGENTS

BACKGROUND OF THE INVENTION

The present invention relates to a method for treating mammals having acquired immunodeficiency syndrome (AIDS) or AIDS-related complex or who are infected with other retroviruses, which comprises the administration of a therapeutically effective amount of a purine or pyrimidine acyclonucleoside. Certain compounds of this class, such as the guanine derivatives, have been found to have activity against the herpes class of viruses such as herpes simplex virus. See European patent application No. 82401571.3. However, it has not been previously shown that these compounds are effective against retroviruses such as human immunodeficiency virus (HIV), the cause of acquired immuno-deficiency syndrome (AIDS) and AIDS related complex.

SUMMARY OF THE INVENTION

It has now been discovered that cyclic monophosphate derivatives of purine and pyrimidine acyclonucleosides have anti-retroviral activity and are useful in the treatment of Acquired immuno-deficiency syndrome (AIDS) and AIDS related complex as well as other retroviral infections. It is a purpose of this invention to show that these compounds have increased potency and/or decreased host toxicity relative to known anti retroviral compounds. It is a purpose of this invention to describe the anti-retroviral acitvity of such compounds. A further purpose is to describe composition containing such compounds as the active ingredient thereof. Further purposes will become apparent from a reading of the following description.

DESCRIPTION OF THE INVENTION

The present invention concerns cyclic monophosphate derivatives of purine and pyrimidine acyclonuleosides which have anti-retroviral activity. The compounds with the novel anti-retroviral activity have the formula B—CH$_2$—X—Z wherein:

B is a purine, a substituted purine, a pyrimidine, or a substituted pyrimidine; wherein the substituents on the purine or pyrimidine are selected from amino, hydroxyl, halogen thio or alkylthio wherein the alkyl moiety of the alkylthio has 1 to 6 carbons;
X is oxygen, sulfur or methylene;
Z is

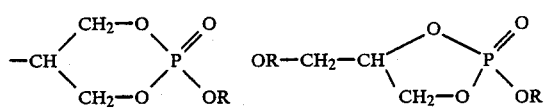

R is hydrogen or a pharmaceutically acceptable cation.

The most preferred compound of this invention is where B is guanine, X is oxygen, Z is;

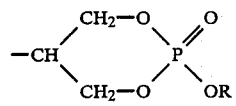

and R is hydrogen or a pharmaceutically acceptable cation.

A preferred compound of this invention is where B is cytosine, X is oxygen, Z is;

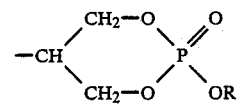

and R is hydrogen or a pharmaceutically acceptable cation. Purines, substituted purines, pyrimidines and substituted pyrimidines are defined as the common heterocyclic bases of nucleic acids and include, but are not limited to adenine, guanine, cytosine, thymine and uracil.

While purines and pyrimidines that are represented by B, as defined above, may be attached to the —CH$_2$—X—Z moieties from various positions on the purines and pyrimidines, the preferred position for the purines is the 9-position and the preferred position for the pyrimidines is the 1-position.

The term "pharmaceutically acceptable cation" refers to those cations which possess the biological effectiveness and properties of the free compound and which are not biologically or otherwise undesirable. Examples of these cations include ions of sodium, potassium, lithium, calcium, magnesium, ammonium, and substituted ammonium, as well as any other acceptable cation known in the art.

Acyclonucleoside cyclic monophosphates are prepared by treating the appropriately substituted and protected or unprotected purine or pyrimidine acyclonucleoside with an excess of a phosphorylating agent such as phosphorus oxychloride or pyrophosphoryl chloride in an inert solvent such as triethyl phosphate and optionally, in the presence of a complexing agent such as SnCl$_4$, to solubilize the reactants. The desired product of this reaction, a cyclic monophosphate, is separated from other products such as the bis monophosphate, by for instance gradient elution from a column of anionic exchange resin.

Halopurines which are used as starting materials in the preparation of compound of the present invention are known in the literature. Halopurine acyclonucleosides are prepared by methods disclosed in European patent application 82401571.3, Publication No. 0 074306, published Mar. 16, 1983; K.K. Ogilvie and M.F. Gillen, Tetrahedron Letters, Vol. 21, 327–330 (1980); and H.J Shaeffer et al., Nature, Vol. 272, 583–585 (1978). The appropriate halopurine acyclonucleosides can be used directly to make the cyclic monophosphates.

Pyrimidine acyclonucleosides with the desired ring substitution are synthesized by literature methods such as disclosed in European patent application 81106460.9, Publication No. 0 046 307, published Feb. 24, 1982; H.M.. Abrams et al., J. Heterocyclic Chem., 18, 947–951 (1981); and K.K. Ogilvie and M.F. Gillen, Tetrahedron Letters, Vol. 1, 327–330 (1980). The pyrimidine acyclonucleosides are phosphorylated by methods disclosed herein and the ring closed to yield cyclic monosphates.

Various tests can be preformed to determine whether a compound has antiretroviral activity. It has been found that Visna virus, a lentivirus of the retorvirus family, has genetic and biological similarities to the human immunodeficiency virus (HIV) which is also a retrovirus. Thus, visna virus is used to test a compounds antiretroviral and anti HIV activity since activity against Visna virus is thought to predict activity against the human immunodeficiency virus.

Acquired immuno-deficiency syndrome (AIDS) is a complex disease state which causes suppression of the body's immune system. The cause of AIDS is thought to be a retrovirus known as the human immunodeficiency virus (HIV). This virus is also known as HTLV-III (human T lymphotrophic virus Type III), lymphadenopathy-associated virus (LAV), or ARV (AIDS-associated retrovirus). HIV has an affinity for lymphocytes, in particular $T_4$ helper lymphocytes. The virus invades normal $T_4$ helper cells and integrates viral genes with normal $T_4$ helper cell genes. This results in an alteration of normal cellular function or death of the $T_4$ helper cell. The ultimate result is suppression of the immune system. This immune system suppression leads to a variety of opportunistic infections which may result in serious illness or death. The opportunistic infections which may result include Pneumocystis Carinii Pneumonia, toxoplasmosis, cytomegalovirus infection, tuberculosis or candidiasis. In addition to these opportunistic infections, mammals infected with HIV frequently develop secondary cancers such as Kaposi's sarcoma, as well as neurological disorders. Mammals who do not develop the full array of symptoms but who are infected with HIV and show mild immune suppression are said to be suffering from AIDS related complex (ARC). Treatment of AIDS and ARC has primarily consisted of the treatment of the opportunistic infections which result from being infected with HIV.

In connection with the use of the compounds of this invention for the treatment of viral infections, it is to be noted that they may be administered either alone or in combination with pharmaceutically acceptable carriers and that such administration can be carried out in both single and multiple dosages. More particularly, a compound of the present invention is administered in an effective unit dosage form.

As used herein the term "effective unit dosage" or "effective unit dose" is denoted to mean a predetermined antiviral amount sufficient to be effective against the virus in vivo. Pharmaceutically acceptable carriers are materials useful for the purpose of administering the medicament, and may be solid, liquid or gaseous materials, which are otherwise inert and medically acceptable and are compatible with active ingredients.

These pharmaceutical compositions may be given parenterally, orally, used as a suppository or pessary, applied topically as an ointment, cream, aerosol, powder, or given as eye or nose drops, etc., depending on whether the preparation is used to treat internal or external viral infections.

For infections the compositions are administered orally or parenterally at dose levels of about 0.1 to 500 mg per kg, preferably 1.0 to 250 mg per kg of mammal body weight, and are used in man in a unit dosage form, administered for example, one to four times daily, in the amount of about 1 to about 1000 mg per unit dose.

For oral administration, fine powders or granules may contain diluting, dispersing and/or surface active agents, and may be presented in a draught, in water or in a syrup; in capsules or sachets in the dry state or in an aqueous or non-aqueous solution or suspension, wherein suspending agents may be included; in tablets, wherein binders and lubricants may be included; or in a suspension in water or a syrup. Where desirable or necessary, flavoring, preserving, suspending, thickening or emulsifying agents may be included. Tablets and granules are preferred, and these may be coated.

For parenteral administration or for administration as drops, as for eye infections, the compounds may be presented in a solution or suspension in a concentration of from about 0.1 to 10%, more preferably 0.1 to 7%, most preferably 0.2% w/v. The solution may contain antioxidants, buffers, etc.

Alternatively, for external infections for example, the mouth or skin, the compositions are preferably applied to the infected part of the body of the patient as a topical ointment or cream. The compounds may be presented in an ointment, for instance, with a water soluble ointment base, or in a cream, for instance with an oil in water cream base, in a concentration of from about 0.1 to 10%, preferably 0.1 to 7%, most preferably 1% w/v.

The compounds of the present invention may also be administered in combination with other antiviral drugs such as azidothymidine (AZT). The compounds of the present invention will form synergistic combinations with these other antiviral agents.

The following examples are included to represent the synthesis of compounds of the present invention as well as their activity against retroviruses. It is intended that the specification and examples be considered as exemplary only, with the true scope and spirit of the invention being indicated by the claims of the invention.

EXAMPLE 1

9-[(2-hydroxy-1,3,2-dioxaphosphorinan 5-yl)oxy-methyl]guanine P-oxide

A suspension of 5.91 g (23.2 mmoles) of anhydrous 9-(1,3 dihydroxy-2-propoxymethyl)-guanine in a solution of 3.6 g (2.2 ml; 23.6 mmoles) of phosphorous oxychloride in 60 ml of anhydrous triethyl phosphate was stirred at room temperature for five hours. The largely clarified mixture was filtered, and the filtrate was poured into 600 ml of stirred hexane. After about five minutes the supernatant hexane was decanted from the precipitated product, and the residue was heated with a second 600 ml portion of hexane. After the supernatant hexane was decanted and the residue was dried in vacuo, 15.9 g of a solid product was obtained. The solid was largely dissolved in 800 ml of deionized water and the cloudy mixture was titrated to pH 7 with 5N potassium hydroxide and then 1N potassium hydroxide. The neutralized mixture was filtered and the filtrate was lyophilized yielding 9.25 g of product.

A specimen of the lyophilization residue was analyzed by high performance liquid chromatography using a Whatman Partisil ™ PXS 10/25 SAX ion exchange column with 0.05M pH 6.6 phosphate buffer elution and ultraviolet absorption detection at 252 nm. The product exhibited three peaks with retention times of about 4 minutes, 7 minutes and 9 minutes. The cyclic monophosphate derivatives was associated with the 4 minute retention time.

The lyophilized mixture of potassium salts was dissolved in 1 liter of deionized water and filtered through a fluted filter paper. The filtrate was slowly passed through a 4–5 cm diameter column of 460 ml (644 milliequivalents) of 200–400 mesh Bio Rad AG1-X8 anion exchange resin on the bicarbonate cycle. Next, a gradient of 0.05M–0.5M potassium bicarbonate from a gradient elution chamber containing 2 liters of 0.05M and 0.5M potassium bicarbonate was pumped through the column and fractions of about 20 ml were collected at 8-minute intervals. At fraction 191, the eluent was changed to 0.5M potassium bicarbonate and samples of 20-25 ml were collected at 6.8-minute intervals. The elution pattern was monitored by ultraviolet absorption at 252 nm and certain component fractions of the various elution peaks were further characterized by high performance liquid chromatography in the Whatman Partisil TM PXS 10/25 SAX ion exchange column using 0.05M pH 6.6 phosphate elution. On the basis of these data certain fractions were combined and worked up as follows:

Fractions 450–540 (1680 ml) characterized by a single peak with a retention time of about 5 minutes in the above high performance liquid chromatography system, were combined and treated with 600 ml (1020 milliequivalents) of 200–400 mesh Bio Rad AG50W-X8 cation exchange resin on the acid cycle. The stirred mixture was kept under a modest vacuum to remove carbon dioxide before it was filtered. The mixture was filtered and the resin was washed with small portions of deionized water. The combined filtrates were concentrated to a 150 ml volume in vacuo at about 35° and the precipitated product, in the form of the free acid, was isolated by filtration and dried in vacuo to yield 445 mg of 9-(1,3-dihydroxy-2-propoxymethyl) guanine cyclic monophosphate. The product was crystalline according to microscopy in polarized light, showed an ultraviolet absorption maximum at 252 nm ($\epsilon$ 10600, in 0.1M pH 7 phosphate), and gave a nuclear magnetic resonance spectrum fully in accord with the projected structure. Concentration of the mother liquors yielded an additional 46 mg of the free acid form of the product. Titration of the mother liquors to pH 7 followed by lyophilization yielded 196 mg of sodium 9-(1,3-dihydroxy-2-propoxy-methyl)guanine cyclic monophosphate. The latter compound, may at times be contaminated with small amounts of water soluble inorganic salts and may be purified by exclusion chromatography or by ion exchange chromatography on Bio Rad AG1-X8 anion exchange resin on the formate cycle.

The pure sodium salt was also obtained by titration of the crystalline free acid as follows:

A suspension of 213 mg of crystalline 9-(1,3-dihydroxy-2-propoxymethyl)guanine cyclic monophosphate was titrated to pH 7 with 1N sodium hydroxide and the solution was lyophilized yielding 227 mg of sodium 9-(1,3-dihydroxy-2-propoxy-methyl)-guanine cyclic monophosphate. A dried sample of this product had an ultraviolet absorption maximum at 252 nm ($\epsilon$ 11800 in 0.1M pH 7 phosphate).

The 200 MHz NMR spectrum of the cyclic product in $D_2O$ is characterized by signals from two equivalent methylenes that have shifted downfield on monophosphorylation. The spectrum is characterized by the following chemical shifts.

| | | | | |
|---|---|---|---|---|
| $\delta$3.94 |  | m | 1H | |
| $\delta$4.25 | P—O—CH eq | d,d,d | 2H | (JH,H gem 12.5 Hz) (JP—OCH eq 19.5 Hz) (JH,H vic eq 2.2 Hz) |
| $\delta$4.39 | P—O—CH$_{ax}$ | d,d,d | 2H | (JH,H gem 12.5 Hz) (JP—OCH ax 5.0 Hz) (JH,H vic ax 1.8 Hz) |
| $\delta$5.64 | N—CH$_2$O | s | 2H | |
| $\delta$7.99 | C$_8$—H | s | 1H | |

Additional confirmation of structure is obtained when the predicted pattern of shifts is realized for the P—O—CH$_2$ groups on irradiation of the

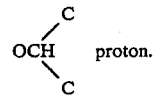 proton.

In a Varian AX 10 high performance liquid chromatography anion exchange column using a gradient of 10–1000 mM unbuffered KH$_2$PO$_4$, the cyclic product has a retention time of 4.3 minutes whereas the enzymically derived acyclic monophosphate has a retention time of 4.8 minutes. The synthetic cyclic monophosphate is clearly separated from the acyclic enzymically-derived monophosphate when a mixture of the two is subjected to HPLC in the above system.

As an alternative, the sodium or potassium salt of the cyclic monophosphate may be isolated from the Bio Rad AG1-X8 bicarbonate eluate fractions without isolation of the crystalline free acid. A combination of fractions amounting to about 800 ml of 0.5M KHCO$_3$ was treated with 325 ml (552 mmoles) of 200–400 mesh AG50W-X8 cation exchange resin on the acid cycle. The stirred mixture was kept under modest vacuum for fifteen minutes to remove carbon dioxide and was filtered. The filtrate was concentrated to about a 100 ml volume which was then titrated to pH 7 with 1N sodium hydroxide. Lyophilization of the resulting solution yielded 529 mg of the sodium salt of the cyclic phosphate that was contaminated with a small amount of water soluble inorganic salts.

To desalt the product, 200 mg of the sodium salt was dissolved in 1.5 ml of deionized water and put on a 1.5 cm diameter column of 6 ml of Bio Rad 200–400 mesh AG1-X8 anion exchange resin on the formate cycle. After about 35 ml of deionized water was passed through the column, elution was begun with 2N ammonium formate solution. Fractions of 3.5 ml volume were collected at 3 minute intervals and the ultraviolet absorption at 250 nm of each fraction was measured and plotted versus tube number. On the basis of the shape of the curve obtained in the above plot, fractions 13–28 were combined and put on a 2-3 cm diameter column of 120 ml (204 milliequivalents) of 200–400 mesh Bio Rad AG50W X8 cation exchange resin. The column was eluted with water and 13.5 ml fractions were collected at 4.5-minute intervals. The elution pattern was monitored by ultraviolet absorption at 252 nm and on the basis of the plot, fractions 22–40 were combined and concentrated to dryness. The residue was taken up in 10 ml of deionized water and titrated to pH 7 with 0.1N NaOH. Lyophilization of the neutralized solution yielded 106 mg of sodium 9-(1,3-dihydroxy-2-propoxymethyl)guanine cyclic monophosphate.

EXAMPLE 2

1-[(2-hydroxy-1,3,2-dioxophosphorinan-5-yl)-oxymethyl]cytosine P-oxide.

To a stirred suspension of 1-[(1,3-dihydroxy-2-propoxy)methyl]cytosine (200 mg 0.93 mmol) in sieve-dried $CH_3CN$ (150 ml) was added $SnCL_4$ (0.15 mL, 1.29 mmol) and dissolution slowly occurred over 1 hour at room temperature. To this stirred solution was added dropwise (over 90 minutes) a solution of pyrophosphoryl chloride (0.4 mL, 2.7 mmol) in $CH_3CN$ (60 ml). After stirring for an additional 2 hours the mixture was neutralized to pH 6.4 by the addition of a saturated solution of $NaHCO_3$ and the mixture was stored in the refrigerator overnight. The solids were filtered off and the filtrate was evaporated to dryness in vacuo. This residue (1.3 g) was dissolved in $H_2O$ (4 mL) and the pH adjusted to 0.35 before being applied to a Darco (20-40 mesh) activated carbon column (12 g). The column was developed with $H_2O$ until no $CL-$ was detected in the washings by the $AgNO_3$ test (~3L) and then with 5% $NH_4OH$ in 50% aqueous EtOH. Fractions containing the title compound were pooled and evaporated to dryness to give 190 mg of crude product as the $NH_4+$ salts. This material was dissolved in $H_2O$ and applied to a Dowex 1×8 (HCOO−form) column (200-400 mesh, 10 mL). The column was developed first with $H_2O$ and then with a linear gradient of $H_2O$ to 2N HCOOH. Fractions containing the required product were pooled and evaporated to dryness several times from $H_2O$, and their lyophilized to give 32 mg of the title compound as a white powder, which was a single peak upon evaluation by HPLC. 2H NMR ($D_2O$ δ from TSP): 3.87 (m, O—CH($CH_2O_2$, 4.17-4.49 (m, $CH_2OP$), 5.36 (S, N—$CH_2$—O), 6.09(d, J=8.0 Hz, $H_5$), 7.66 (d, J=8.0 Hz, $H_6$).

Anal. Calc. for $C_8H_{12}N_3O_6$ P. 1.2 $H_2O$: C, 32.16; H, 4.86; N, 14.06.

Found: C, 31.97; H, 4.55; N, 13.81.

EXAMPLE 3

Activity of 9-[(2-hydroxy-1,3,2-dioxophosphorian-5-yl)oxymethyl]guanine P-oxide, sodium salt (2'-NOR-cGMP) against visna virus in sheep choroid plexus cells.

Visna virus, strain 1514, is a lentivirus of the retrovirus family. It was chosen because of its genetic and biologic similarity to the human immunodeficiency viruses (HIV). Since visna virus and the human immunodeficiency virus are closely related retroviruses, activity against the visna virus by a compound is felt to predict activity against the human immunodeficiency virus by the same compound. (See Visna Virus as an In Vitro Model for Human Immunodeficiency Virus and Inhibition by Ribavirin, Phosphonoformate, and 2',3'-Dideoxy-nucleosides, Frank K. B.; McKernan P.A.; Smith R.A.; Smee D.F.; Antimicrobiol Agents and Chemotherapy, Sept. 1987; Vol. 31, No. 9 Pg 1369-1374.) The virus has been cultivated and plaque purified in SCP cells fed with MEM, HEPES, gentamicin and 2% lamb serum.

Visna virus is cultivated in low passage cells derived from the choroid plexus (SCP) of a newborn lamb. The choroid plexus is dissected from the newborn lamb, minced and diluted in minimum essential medium (MEM), containing 20% fetal bovine serum (FBS), 1 mM N 2-hydroxyethylpiperazine-N'-2-ethane sulfonic acid (HEPES), 50 µg/ml gentamicin at PH 7.4. After initial cultivation, cells are dispersed by addition of trypsin (0.25%) plus EDTA, split 1:2 and added to MEM+10% FBS, HEPES, gentamicin and reincubated. At approximately passage 4 there are adequate numbers of cells for freezing and storage in liquid nitrogen.

For antiviral assays, 0.2 ml SCP cells ($0.7 \times 10^5$ cells/ml) are inoculated into wells of 96 well microtiter plates and incubated for 18-24 hours.

The medium is decanted from the cells, and drug and virus(~320-50% infectious doses) are added within 15 minutes. Each concentration of drug (serial two-fold or half-log dilutions) are added in 0.1 ml volumes to each of 6 wells. Visna virus is added (0.1 ml) to 4 wells for observation of virus inhibitory activity.

Virus free test medium is added to two wells (0.1 mL) for observation of drug cytotoxicity. Experimental controls include: cell control (cells with 0.2 mL medium) and virus controls (cells with 0.1 mL virus and 0.1 mL medium). The degree of CPE inhibition and drug cytotoxicity in comparison with virus and cell controls is observed microscopically after 6 days of incubation at 37° C. Fresh medium and drug dilutions are placed on the cells after 3 days of incubation. Virus CPE and drug cytotoxicity are scored on a 0-4 basis with 4 representing total cell destruction. The lowest concentration of drug producing ≧50% inhibition of virus-induced CPE is considered the minimum inhibitory concentration (MIC). The lowest concentration of drug producing a score of ≦1 or visable alteration in cell morphology will be considered the minimum cytotoxic concentration (MCC). Using the observed percent CPE, the MIC will be calculated by linear regression analysis.

The following chart shows the effect various antiviral agents, including 2'-nor-cGMP, has on visna virus in sheep choroid plexus cells.

|  | Range of Concentrations Tested (µg/mL) | MIC[1] (µg/mL) Individual Values | Mean | MCC[2] (µg/ml) Individual Values | Range |
| --- | --- | --- | --- | --- | --- |
| 2'-nor-cGMP | 100-0.1 | 18.3,27.0,26.7 | 24.0 | 33.32,100 | 32-100 |
| Virazole | 1000-1.0 | 141.3,219.9, 192.3,147.3 | 175.3 | 320,100, 320,100 | 100-320 |
| Phosphonoformate | 100-0.1 | 60.9,57.8 | 57.4 | 100,100 | 100 |
| Azidothymidine | 40-0.625 | 10.0 | 10.0 | 40 | 40 |

[1]MIC—minimum inhibitry concentration
[2]MCC—minimum cytotoxic concentration

What is claimed is:

1. A method for the treatment of a mammal having acquired immuno-deficiency syndrome (AIDS) or AIDS related complex or lentivirus retroviruses, which comprises the administration to the mammal of a therapeutically effective amount, sufficient to inhibit suppression of the mammal's immune system, of a compound having the formula B—CH₂—X—Z, wherein B is guanine, X is oxygen, and Z is
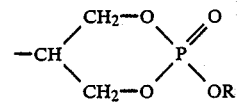
an R is hydrogen or a pharmaceutically acceptable cation.
2. A method of claim 1, wherein the compound is 9-[(2-hydroxy-1, 3, 2-dioxophosphorian-5-yl)-oxymethyl] guanine P-oxide.
* * * * *